(12) United States Patent
Huang et al.

(10) Patent No.: US 11,927,578 B2
(45) Date of Patent: Mar. 12, 2024

(54) SMART WEARABLE DEVICE

(71) Applicant: RADIANT INNOVATION INC., Hsinchu County (TW)

(72) Inventors: Yu-Chien Huang, Hsinchu (TW); Chien-Chang Liao, Hsinchu (TW)

(73) Assignee: RADIANT INNOVATION INC., Hsinchu County (TW)

( * ) Notice: Subject to any disclaimer, the term of this patent is extended or adjusted under 35 U.S.C. 154(b) by 329 days.

(21) Appl. No.: 17/554,021

(22) Filed: Dec. 17, 2021

(65) Prior Publication Data

US 2023/0194491 A1   Jun. 22, 2023

(51) Int. Cl.
*G01N 33/00* (2006.01)
*G01P 13/00* (2006.01)
*G06F 3/14* (2006.01)
*G06T 13/00* (2011.01)
*G08B 6/00* (2006.01)
*G08B 21/12* (2006.01)
*G08B 21/18* (2006.01)
*G10H 1/00* (2006.01)
*H04Q 9/00* (2006.01)
*H04R 1/02* (2006.01)

(52) U.S. Cl.
CPC .......... *G01N 33/0036* (2013.01); *G01P 13/00* (2013.01); *G06F 3/14* (2013.01); *G06T 13/00* (2013.01); *G08B 6/00* (2013.01); *G08B 21/12* (2013.01); *G08B 21/182* (2013.01); *G10H 1/0008* (2013.01); *H04Q 9/00* (2013.01); *H04R 1/028* (2013.01); *H04Q 2209/40* (2013.01)

(58) Field of Classification Search
None
See application file for complete search history.

(56) References Cited

U.S. PATENT DOCUMENTS

2017/0186298 A1\* 6/2017 Wang ................... G08B 21/182
2018/0231515 A1\* 8/2018 Voumard ............. G04G 9/0005

\* cited by examiner

*Primary Examiner* — Brandi N Hopkins
*Assistant Examiner* — Nigel H Plumb
(74) *Attorney, Agent, or Firm* — Li & Cai Intellectual Property (USA) Office

(57) ABSTRACT

A smart wearable device includes a wearable device body, a signal control module, a gas detection module, a signal recording module, and a vibration generating module. The gas detection module can detect a gas concentration of a predetermined gas surrounding the wearable device body so as to obtain a gas concentration signal. The signal recording module can record a plurality of gas concentration values that are provided by the gas concentration signal, and record a plurality of gas-measuring time points that are respectively configured for obtaining the gas concentration values. The vibration generating module can generate a prompt signal according to the gas concentration value provided by the gas concentration signal, and generate a beat signal according to a user setting value. Therefore, the smart wearable device can provide relevant information corresponding to the gas concentration signal, the prompt signal, and the beat signal for a user.

10 Claims, 11 Drawing Sheets

SMART WEARABLE DEVICE

FIELD OF THE DISCLOSURE

The present disclosure relates to a wearable device, and more particularly to a smart wearable device.

BACKGROUND OF THE DISCLOSURE

A conventional smart wearable device can provide relevant information for a user, but still has room for improvement in the related art.

SUMMARY OF THE DISCLOSURE

In response to the above-referenced technical inadequacy, the present disclosure provides a smart wearable device.

In one aspect, the present disclosure provides a smart wearable device, which includes a wearable device body, a signal control module, a gas detection module, a signal recording module, a vibration generating module, a signal display module, an audio generating module, a motion sensing module, and a wireless transmission module. The signal control module is disposed on the wearable device body. The gas detection module is disposed on the wearable device body and electrically connected to the signal control module. The gas detection module is configured to detect a gas concentration of a predetermined gas surrounding the wearable device body so as to obtain a gas concentration signal. The signal recording module is disposed on the wearable device body and electrically connected to the signal control module. The signal recording module is configured to record a plurality of gas concentration values that are provided by the gas concentration signal, and record a plurality of gas-measuring time points that are respectively configured for obtaining the gas concentration values. The vibration generating module is disposed on the wearable device body and electrically connected to the signal control module. The vibration generating module is configured to generate a prompt signal according to the gas concentration value provided by the gas concentration signal, and generate a beat signal according to a user setting value. The signal display module is disposed on the wearable device body and electrically connected to the signal control module, and the signal display module is configured to provide a display signal according to the gas concentration signal. The audio generating module is disposed on the wearable device body and electrically connected to the signal control module, and the audio generating module is configured to provide an audio signal according to the gas concentration signal. The motion sensing module is disposed on the wearable device body and electrically connected to the signal control module, and the motion sensing module is configured to provide a user motion signal according to a user motion trajectory of a user that wears the smart wearable device. The wireless transmission module is disposed on the wearable device body and electrically connected to the signal control module, and the wireless transmission module is configured to wirelessly transmit the gas concentration signal and the user motion signal to at least one electronic device.

In another aspect, the present disclosure provides a smart wearable device, which includes a wearable device body, a signal control module, a gas detection module, a signal recording module, and a vibration generating module. The signal control module is disposed on the wearable device body. The gas detection module is disposed on the wearable device body and electrically connected to the signal control module. The gas detection module is configured to detect a gas concentration of a predetermined gas surrounding the wearable device body so as to obtain a gas concentration signal. The signal recording module is disposed on the wearable device body and electrically connected to the signal control module. The signal recording module is configured to record a plurality of gas concentration values that are provided by the gas concentration signal, and record a plurality of gas-measuring time points that are respectively configured for obtaining the gas concentration values. The vibration generating module is disposed on the wearable device body and electrically connected to the signal control module. The vibration generating module is configured to generate a prompt signal according to the gas concentration value provided by the gas concentration signal, and generate a beat signal according to a user setting value.

Therefore, in the smart wearable device provided by the present disclosure, by virtue of "the gas detection module being disposed on the wearable device body and electrically connected to the signal control module, for detecting a gas concentration of a predetermined gas surrounding the wearable device body so as to obtain a gas concentration signal", "the signal recording module being disposed on the wearable device body and electrically connected to the signal control module, for recording a plurality of gas concentration values that are provided by the gas concentration signal, and recording a plurality of gas-measuring time points that are respectively configured for obtaining the gas concentration values," and "the vibration generating module being disposed on the wearable device body and electrically connected to the signal control module, for generating a prompt signal according to the gas concentration value provided by the gas concentration signal, and generating a beat signal according to a user setting value," the smart wearable device can be configured to provide relevant information corresponding to the gas concentration signal, the prompt signal, and the beat signal for a user wearing the smart wearable device.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
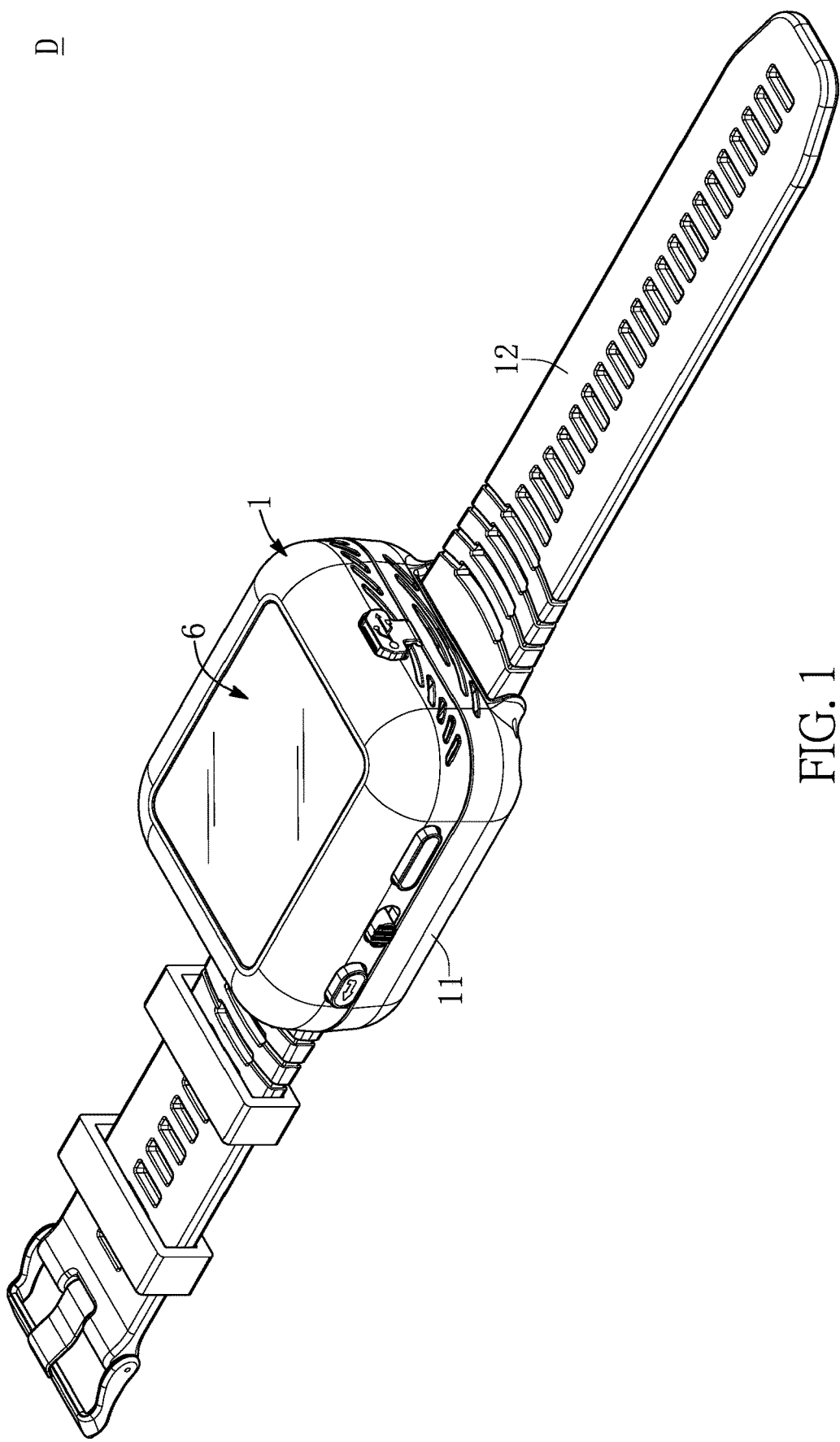
FIG. 1 is a schematic perspective view of a smart wearable device according to an embodiment of the present disclosure.
Figure 2:
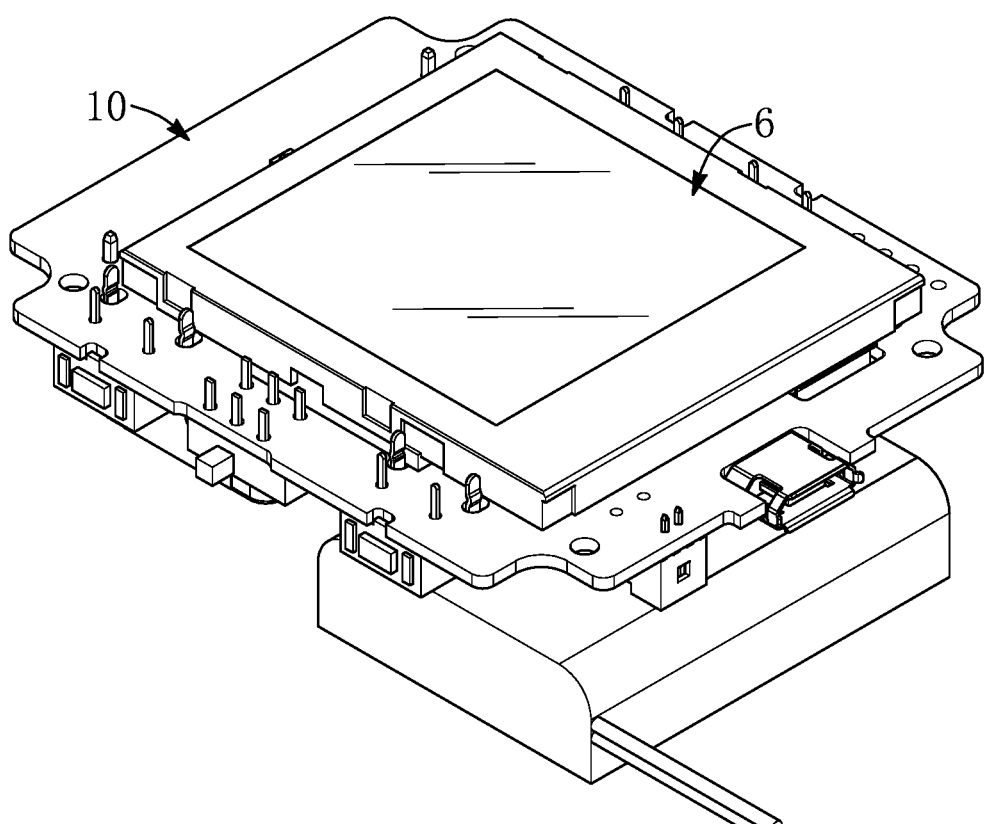
FIG. 2 is a schematic perspective view of a signal display module that is disposed on the smart wearable device according to the embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 10, the present disclosure provides a smart wearable device D, which includes a wearable device body 1, a signal control module 2, a gas detection module 3, a signal recording module 4, and a vibration generating module 5. More particularly, the signal control module 2 is disposed on the wearable device body 1. The gas detection module 3 is disposed on the wearable device body 1 and electrically connected to the signal control module 2, and the gas detection module 3 can be configured to detect a gas concentration of a predetermined gas surrounding the wearable device body 1 so as to obtain a gas concentration signal S1. The signal recording module 4 is disposed on the wearable device body 1 and electrically connected to the signal control module 2, and the signal recording module 4 can be configured to record a plurality of gas concentration values C that are provided by the gas concentration signal S1, and record a plurality of gas-measuring time points T that are respectively configured for obtaining the gas concentration values C by detecting the gas concentration of the predetermined gas. The vibration generating module 5 is disposed on the wearable device body 1 and electrically connected to the signal control module 2, and the vibration generating module 5 can be configured to generate a prompt signal S2 according to the gas concentration value C that is provided by the gas concentration signal S1, and generate a beat signal S3 according to a user setting value. Therefore, when the smart wearable device D is worn by a user, the smart wearable device D can be configured to provide relevant information corresponding to the gas concentration signal S1, the prompt signal S2 and the beat signal S3 for the user.

Embodiments

Referring to FIG. 1 to FIG. 10, one embodiment of the present disclosure provides a smart wearable device D, which includes a wearable device body 1, a signal control module 2, a gas detection module 3, a signal recording module 4, a vibration generating module 5, a signal display module 6, an audio generating module 7, a motion sensing module 8, and a wireless transmission module 9.

More particularly, referring to FIG. 1 to FIG. 4, the signal control module 2 is disposed on (or inside) the wearable device body 1. For example, at least one circuit substrate 10 is disposed inside the wearable device body 1, and the wearable device body 1 has a device casing 11 (such as a watch case) and a watch bracelet 12 connected to the device casing 11. In addition, the signal control module 2 is disposed on the circuit substrate 10 and electrically connected to the circuit substrate 10, and the signal control module 2 can be a central processing unit (CPU), a digital signal process (DSP), a micro processor unit (MPU), or a micro control unit (MCU), etc. However, the aforementioned description is merely an example, and is not meant to limit the scope of the present disclosure.

Figure 3:
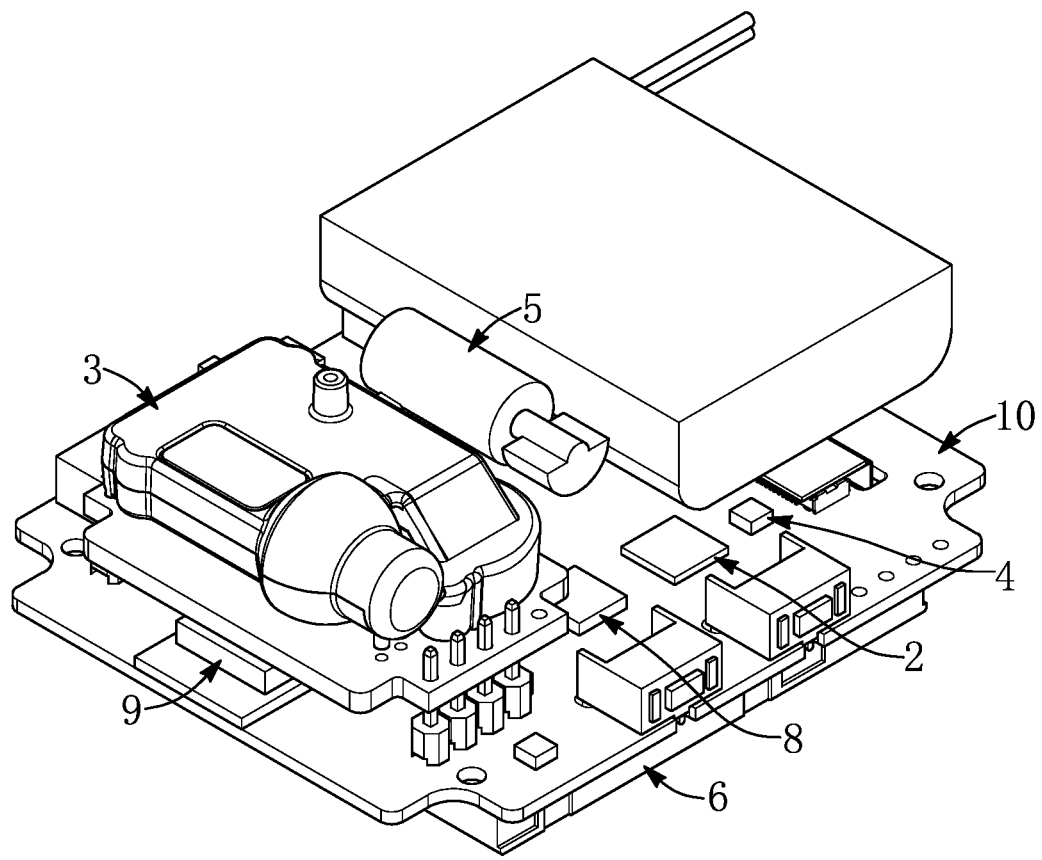
FIG. 3 is a schematic perspective view of a signal control module, a gas detection module, a signal recording module, a vibration generating module, a motion sensing module, and a wireless transmission module that are disposed on the smart wearable device according to the embodiment of the present disclosure.
Figure 4:
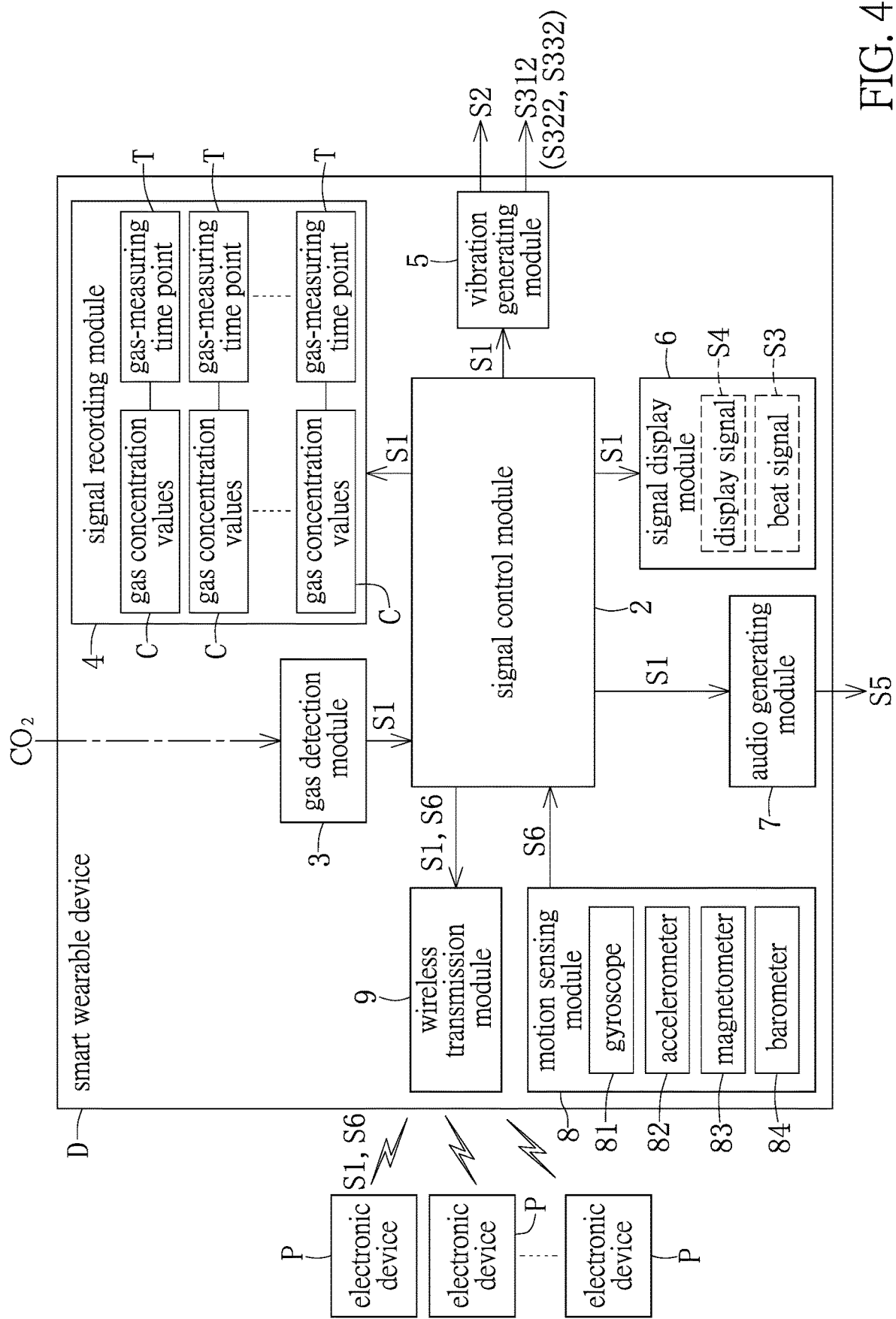
FIG. 4 is a functional block diagram of the smart wearable device according to the embodiment of the present disclosure.

More particularly, referring to FIG. 3 and FIG. 4, the gas detection module 3 is disposed on (or inside) the wearable device body 1 and electrically connected to the signal control module 2, and the gas detection module 3 can be configured to detect a gas concentration of a predetermined gas (i.e., an ambient gas) surrounding the wearable device body 1 (or the smart wearable device D) so as to obtain a gas concentration signal S1. For example, the gas detection module 3 is disposed on the circuit substrate 10 and electrically connected to the circuit substrate 10. In addition, the gas detection module 3 includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal. Therefore, a gas concentration of a predetermined gas (for example, the $CO_2$, $O_2$, CO, $CH_4$, or $NH_3$) surrounding the smart wearable device D can be detected by the gas detection module 3. However, the aforementioned description is merely an example, and is not meant to limit the scope of the present disclosure.

Figure 5:
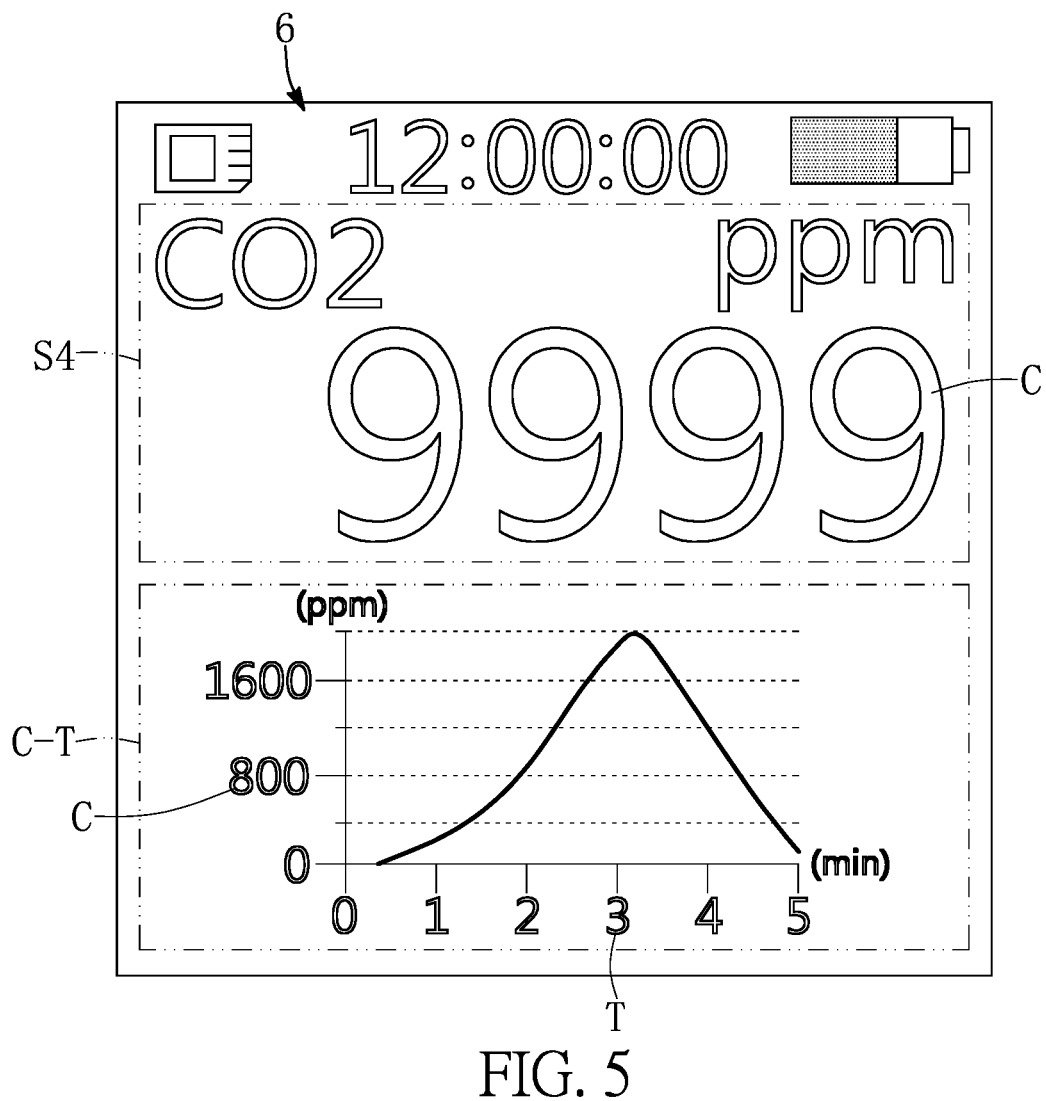
FIG. 5 is a schematic view of the signal display module of the smart wearable device for displaying concentration and time trajectory information and a display signal according to the embodiment of the present disclosure.

More particularly, referring to FIG. 3 to FIG. 5, the signal recording module 4 is disposed on (or inside) the wearable device body 1 and electrically connected to the signal control module 2, and the signal recording module 4 can be configured to record a plurality of gas concentration values C that are provided by the gas concentration signal S1, and record a plurality of gas-measuring time points T that are respectively configured for obtaining the gas concentration values C by detecting the gas concentration of the predetermined gas. For example, the signal recording module 4 is disposed on the circuit substrate 10 and electrically connected to the circuit substrate 10, and the signal recording module 4 can be a static random access memory (SRAM), or a dynamic random access memory (DRAM), etc. In addition, as shown in FIG. 5, when the gas concentration values C (as shown on the Y-axis (parts per million, ppm)) and the gas-measuring time points T (as shown on the X-axis, such as 5 min) match with each other to form a concentration and time trajectory information C-T (or temporal trajectory information) that can be shown on the signal display module 6. Therefore, the user can determine a gas concentration change trend of the environment in which the user stays for a predetermined time range according to the concentration and time trace information C-T that is displayed by the signal display module 6. However, the aforementioned description is merely an example, and is not meant to limit the scope of the present disclosure.

More particularly, referring to FIG. 3 and FIG. 4, the vibration generating module 5 is disposed on (or inside) the wearable device body 1 and electrically connected to the signal control module 2, and the vibration generating module 5 can be configured to generate a prompt signal S2 (or a warning signal) according to the gas concentration value C provided by the gas concentration signal S1. For example, the vibration generating module 5 is disposed on the circuit substrate 10 and electrically connected to the circuit substrate 10, and the vibration generating module 5 includes a micro motor (not shown) and an eccentric wheel (not shown) connected to the micro motor. In addition, when the gas concentration value C provided by the gas concentration signal S1 is less than a first preset value (for example, the $CO_2$ concentration is less than 1000 ppm), the prompt signal S2 generated by the vibration generating module 5 is an unvibrated signal that is configured to stop generating vibration by the vibration generating module 5 (that is to say, the vibration generating module 5 is not vibrated). In addition, when the gas concentration value C provided by the gas concentration signal S1 is greater than the first preset value and less than a second preset value (for example, the $CO_2$ concentration is greater than 1000 ppm and less than 2000 ppm), the prompt signal S2 generated by the vibration generating module 5 is a weak vibration or a short vibration that can be generated by controlling the vibration generating module 5. Moreover, when the gas concentration value C provided by the gas concentration signal S1 is greater than the second preset value (for example, the $CO_2$ concentration is greater than 2000 ppm), the prompt signal S2 generated by the vibration generating module 5 is a strong vibration or a long vibration that can be generated by controlling the vibration generating module 5. That is to say, the vibration intensity (or the vibration magnitude) that is generated by the vibration generating module 5 can be increased according to (or following) the increase of the gas concentration value C, or the vibration length (or the vibration time) that is generated by the vibration generating module 5 can be increased according to (or following) the increase of the gas concentration value C. However, the aforementioned description is merely an example, and is not meant to limit the scope of the present disclosure.

Figure 6:
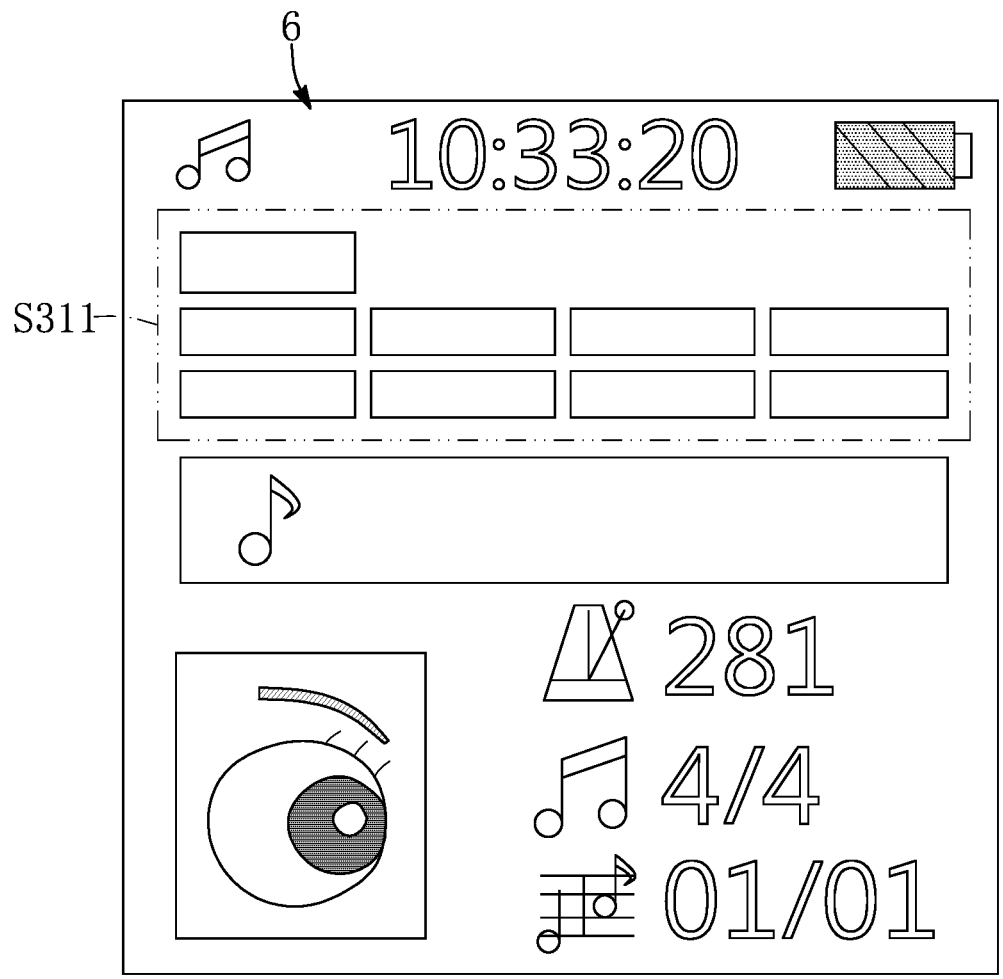
FIG. 6 is a schematic view of the signal display module of the smart wearable device for displaying a musical beat message according to the embodiment of the present disclosure.
Figure 7:
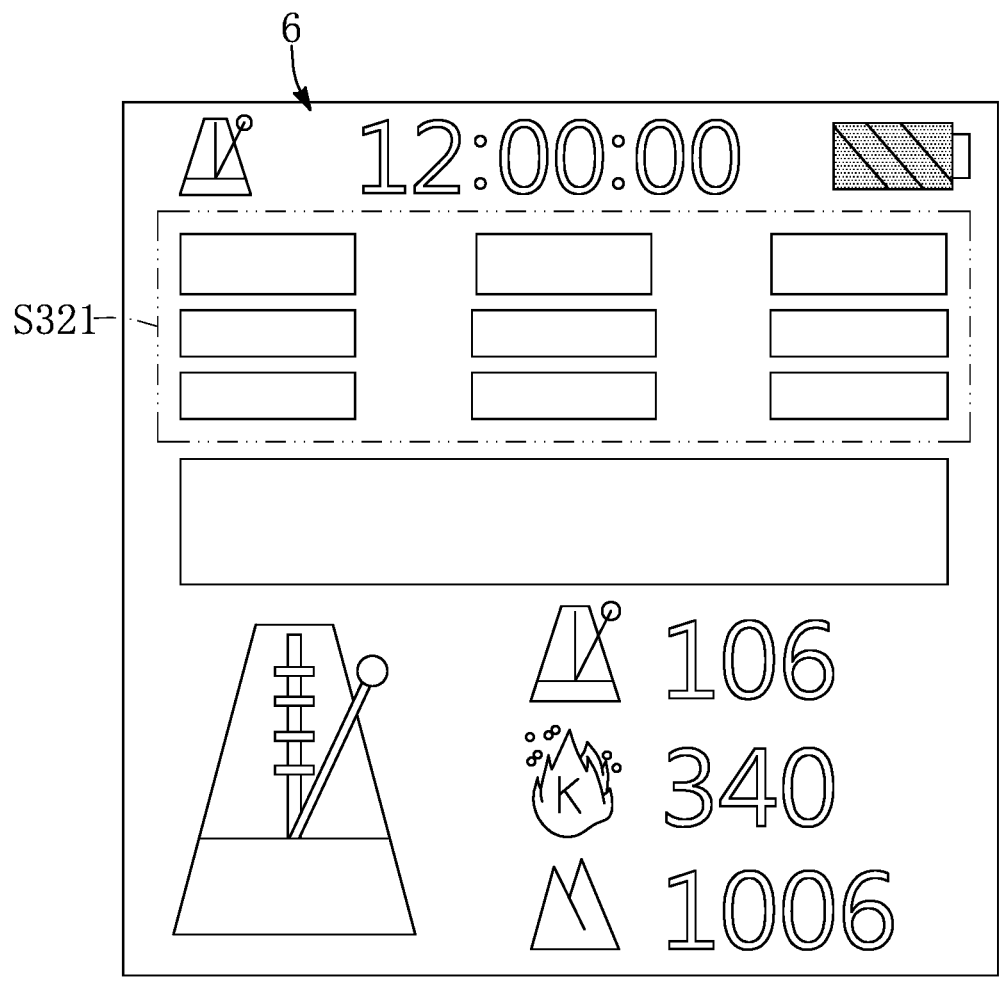
FIG. 7 is a schematic view of the signal display module of the smart wearable device for displaying a rhythmic beat message according to the embodiment of the present disclosure.
Figure 8:
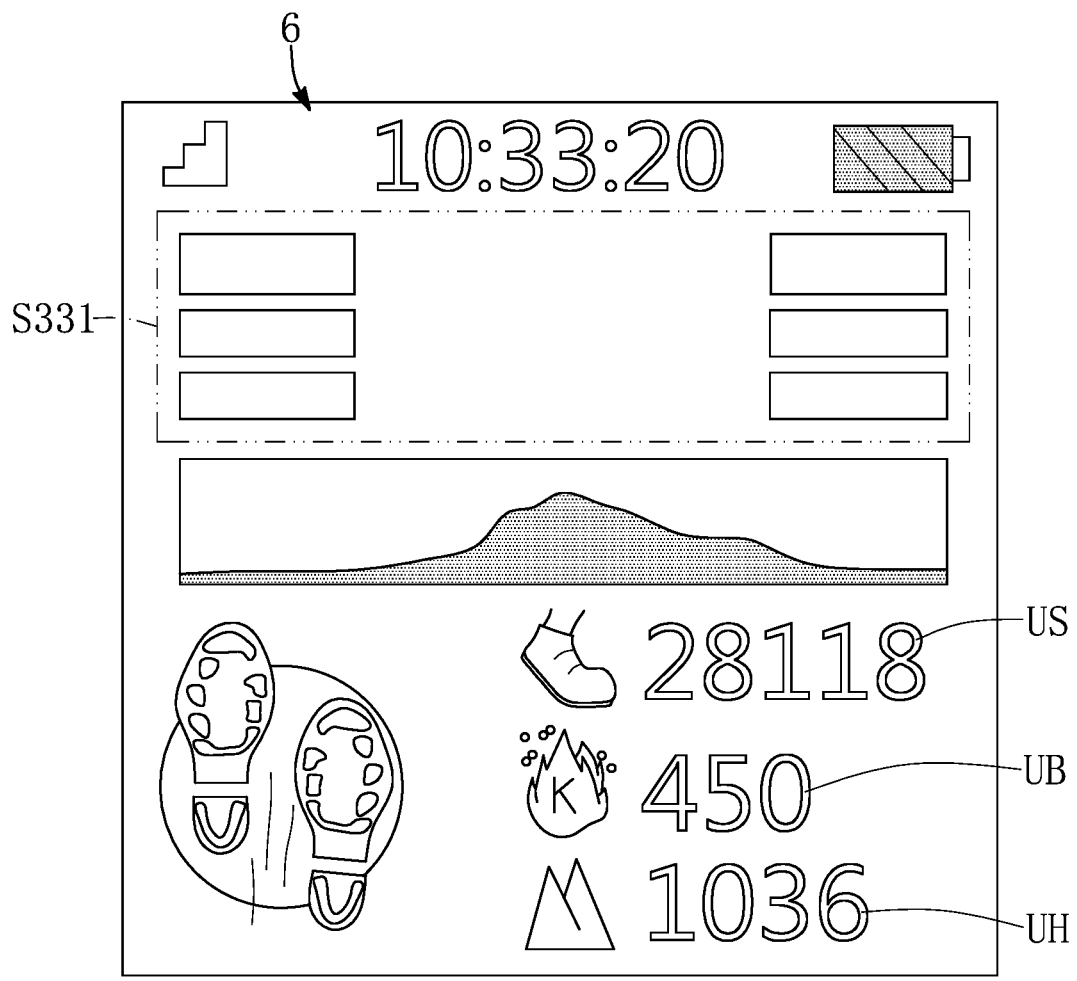
FIG. 8 is a schematic view of the signal display module of the smart wearable device for displaying a walking beat message, a user walking number, a user height value, and user calorie consumption according to the embodiment of the present disclosure.

It should be noted that, referring to FIG. 4 and FIG. 6 to FIG. 8, the vibration generating module 5 can be configured to generate a beat signal S3 according to a user setting value. For example, referring to FIG. 4 and FIG. 6, when the user setting value is set according to music information, the beat signal S3 provided by the vibration generating module 5 includes a musical beat message S311 that can be displayed by the signal display module 6, and a musical beat vibration S312 that can be generated by controlling the vibration generating module 5. More particularly, as shown in FIG. 6, a number of straight columns (such as four straight columns respectively presenting four beats) can be shown as a vibration frequency, and a number of transverse bars of each straight column can be shown as a vibration intensity variation (such as the four straight columns respectively presenting a strong beat (including three transverse bars), a weak beat (including two transverse bars), a weak beat (including two transverse bars), and a weak beat (including two transverse bars). Moreover, referring to FIG. 4 and FIG. 7, when the user setting value is set according to rhythm information, the beat signal S3 provided by the vibration generating module 5 includes a rhythmic beat message S321 that can be displayed by the signal display module 6, and a rhythmic beat vibration S322 that can be generated by controlling the vibration generating module 5. More particularly, as shown in FIG. 7, a number of straight columns (such as three straight columns respectively presenting three beats) can be shown as a vibration frequency, and a number of transverse bars of each straight column can be shown as a vibration intensity variation (such as the three straight columns respectively presenting a strong beat (including three transverse bars), a strong beat (including three transverse bars), and a strong beat (including three transverse bars). Furthermore, referring to FIG. 4 and FIG. 8, when the user setting value is set according to walking information, the beat signal S3 provided by the vibration generating module 5 includes a walking beat message S331 that can be displayed by the signal display module 6, and a walking beat vibration S332 that can be generated by controlling the vibration generating module 5. More particularly, as shown in FIG. 8, a number of straight columns (such as two straight columns respectively presenting two beats) can be shown as a vibration frequency, and a number of transverse bars of each straight column can be shown as a vibration intensity variation (such as the two straight columns respectively presenting a strong beat (including three transverse bars), and a strong beat (including three transverse bars). However, the aforementioned description is merely an example, and is not meant to limit the scope of the present disclosure.

Figure 11:
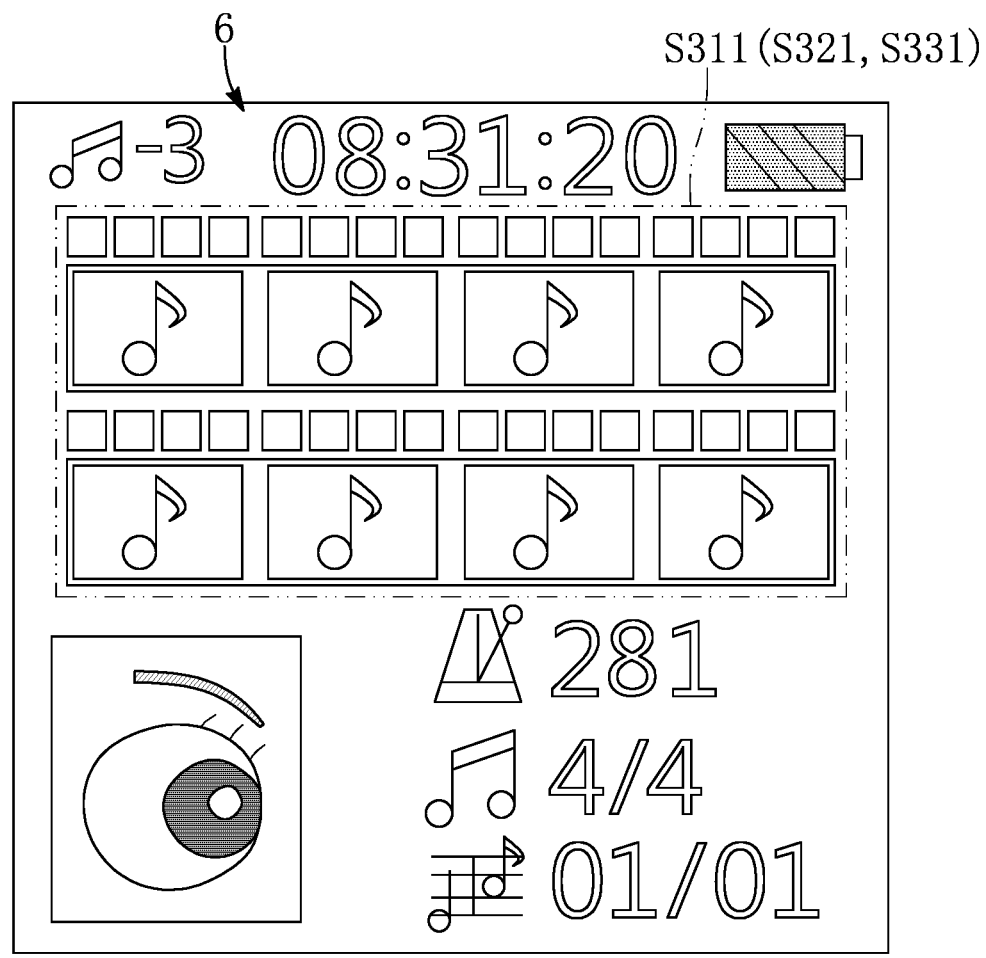
FIG. 11 is a schematic view of the signal display module of the smart wearable device for displaying another musical beat message, another rhythmic beat message, and another walking beat message according to the embodiment of the present disclosure.

It should be noted that, for example, referring to FIG. 6, FIG. 7, FIG. 8 and FIG. 11, the musical beat message S311 as shown in FIG. 6, the rhythmic beat message S321 as shown in FIG. 7, or the walking beat message S331 as shown in FIG. 8 can be replaced by another musical beat message S311, another rhythmic beat message S321, or another walking beat message S331 as shown in FIG. 11. In addition, the another musical beat message S311, the another rhythmic beat message S321, or the another walking beat message S331 as shown in FIG. 11 can be configured for providing a visual music beat, a visual rhythm beat, or a visual walking beat by sequentially lighting different regions (such as sequentially lighting eight notes as shown in FIG. 8) according to different beat settings.

More particularly, referring to FIG. 1 to FIG. 5, FIG. 9 and FIG. 10, the signal display module 6 is disposed on the wearable device body 1 and electrically connected to the signal control module 2, and the signal display module 6 can be configured to provide a display signal S4 according to the gas concentration signal S1. For example, referring to FIG. 2, FIG. 4, FIG. 5 and FIG. 9, the signal display module 6 is disposed on the circuit substrate 10 and electrically connected to the circuit substrate 10, and the signal display module 6 can be configured to display the gas concentration value C of the gas concentration signal S1 that is detected by the gas detection module 3. In addition, as shown in FIG. 5, when the gas concentration values C and the gas-measuring time points T match with each other to form concentration and time trajectory information C-T, the signal display module 6 can be configured to display the concentration and time trajectory information C-T so as to determine a gas concentration change trend of the environment in which the user stays for a predetermined time range. However, the aforementioned description is merely an example, and is not meant to limit the scope of the present disclosure.

Figure 9:
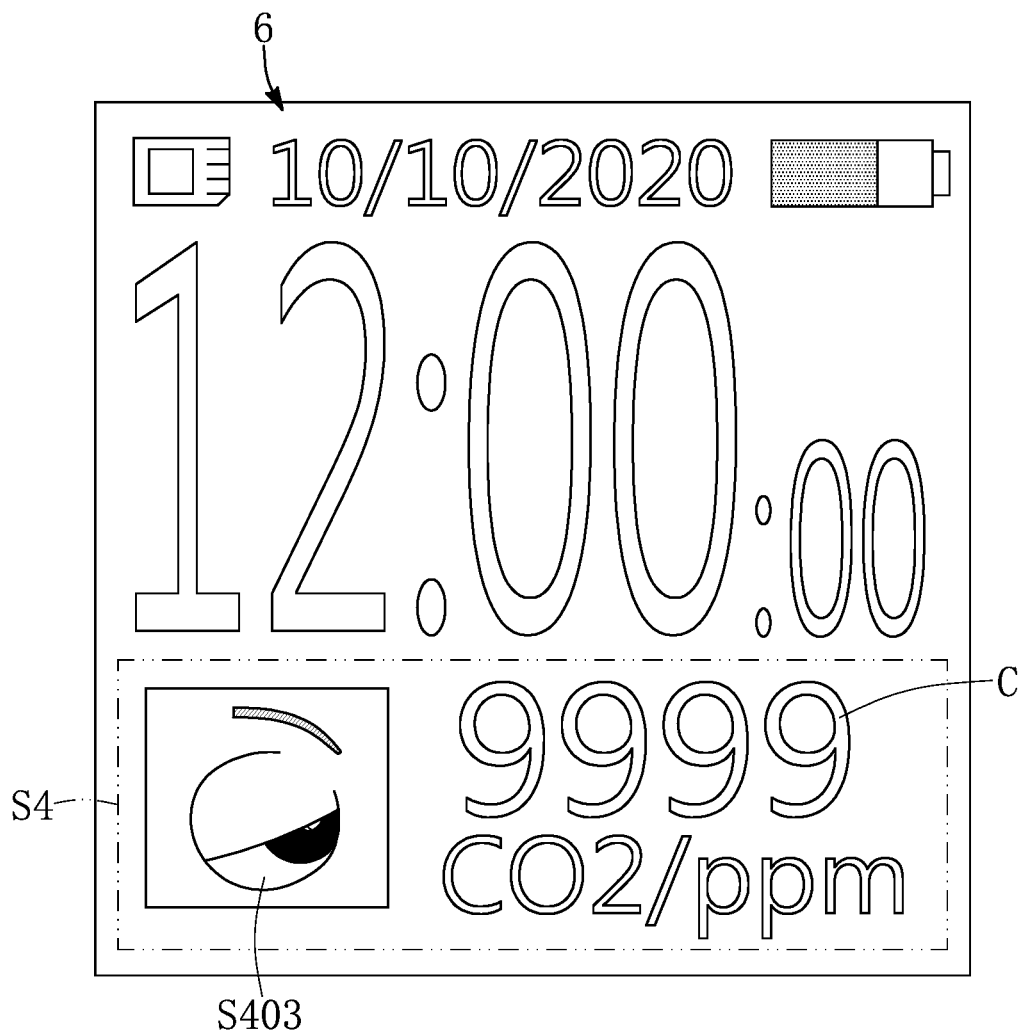
FIG. 9 is a schematic view of the signal display module of the smart wearable device for displaying a third animation message and a gas concentration value according to the embodiment of the present disclosure.
Figure 10:
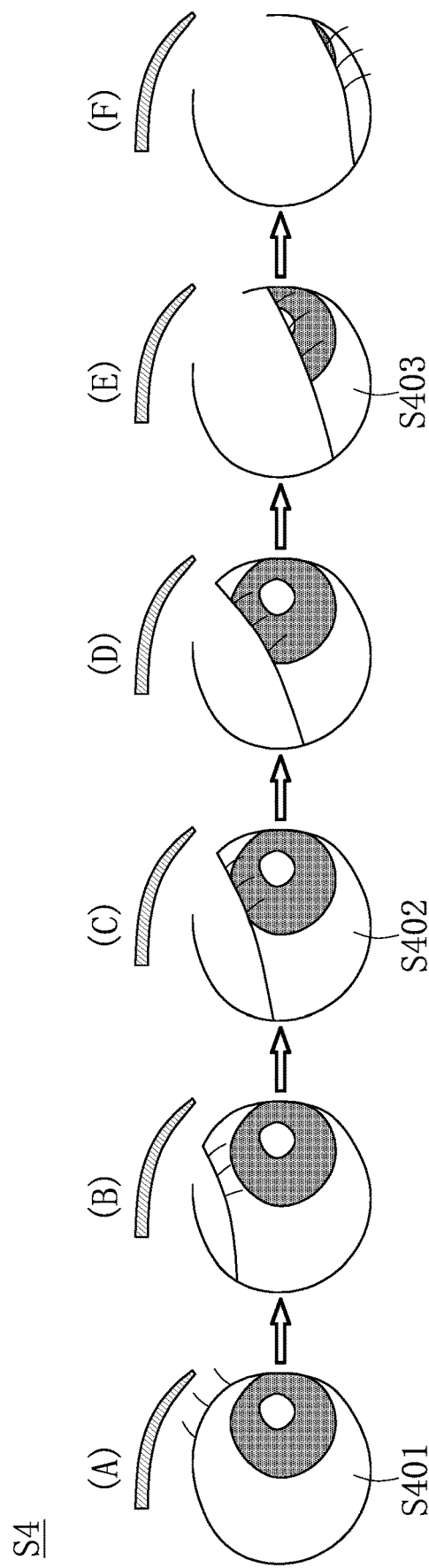
FIG. 10 is a schematic view of a display signal for presenting a plurality of blinking animations (such as a first, a second and a third blinking animation) according to the embodiment of the present disclosure.

For example, referring to FIG. 9 and FIG. 10, when the gas concentration value C provided by the gas concentration signal S1 is less than a first preset value (for example, the $CO_2$ concentration is less than 1000 ppm), the display signal S4 generated by the signal display module 6 includes a first color message (such as a safety color: green), a first animation message S401 (such as a first blinking animation (i.e., closing and opening eye once) as shown in (A) of FIG. 10), or a first combined message (such as a green first blinking animation). In addition, referring to FIG. 9 and FIG. 10, when the gas concentration value C provided by the gas concentration signal S1 is greater than the first preset value and less than a second preset value (for example, the $CO_2$ concentration is greater than 1000 ppm and less than 2000 ppm), the display signal S4 generated by the signal display module 6 includes a second color message (such as a warning color: yellow), a second animation message S402 (such as a second blinking animation as shown in (C) of FIG. 10), or a second combined message (such as a yellow second blinking animation). Furthermore, referring to FIG. 9 and FIG. 10, when the gas concentration value C provided by the gas concentration signal S1 is greater than the second preset value (for example, the $CO_2$ concentration is greater than 2000 ppm), the display signal S4 generated by the signal display module 6 includes a third color message (such as a dangerous color: red), a third animation message S403 (such as a third blinking animation as shown in (E) of FIG. 10), or a third combined message (such as a red third blinking animation). It should be noted that, as shown in FIG. 10, the blinking animations provided by the display signal S4 are respectively presented from (A) to (F) of FIG. 10, and the eye opening percentage of the blinking animation is gradually decreased from (A) to (F) of FIG. 10. That is to say, the eye opening percentage of the first blinking animation of the first animation message S401 is greater than the eye opening percentage of the second blinking animation of the second animation message S402, and the eye opening percentage of the second blinking animation of the second animation message S402 is greater than the eye opening percentage of the third blinking animation of the third animation message S403. However, the aforementioned description is merely an example, and is not meant to limit the scope of the present disclosure.

More particularly, referring to FIG. 1, FIG. 3, FIG. 4 and FIG. 8, the audio generating module 7 is disposed on (or inside) the wearable device body 1 and electrically connected to the signal control module 2, and the audio generating module 7 can be configured to provide an audio signal S5 according to the gas concentration signal S1. Moreover, the motion sensing module 8 is disposed on (or inside) the wearable device body 1 and electrically connected to the signal control module 2, and the motion sensing module 8 can be configured to provide a user motion signal S6 according to a user motion trajectory of a user that wears the smart wearable device D. For example, the audio generating module 7 and the motion sensing module 8 are disposed on the circuit substrate 10 and electrically connected to the circuit substrate 10. In addition, the motion sensing module 8 includes a gyroscope 81, an accelerometer 82 (or an acceleration transducer), a magnetometer 83, and a barometer 84 (or a barometric pressure sensor). In addition, the motion sensing module 8 can be configured to provide a user walking number US (i.e., a walking number of paces that are detected by the accelerometer 82) and a user height value UH (i.e., a height of the user's location that is detected by the barometer 84) according to the user motion trajectory of the user that wears the smart wearable device D, and the signal control module 2 can be configured to obtain user calorie consumption UB of the user that wears the smart wearable device D according to the user walking number US and the user height value UH. That is to say, as shown in FIG. 6, the user motion signal S6 at least includes the user walking number US, the user height value UH, and the user calorie consumption UB. However, the aforementioned description is merely an example, and is not meant to limit the scope of the present disclosure.

More particularly, referring to FIG. 1 and FIG. 4, the wireless transmission module 9 is disposed on (or inside) the wearable device body 1 and electrically connected to the signal control module 2, and the wireless transmission module 9 can be configured to wirelessly transmit the gas concentration signal S1 and the user motion signal S6 to at least one electronic device P or a plurality of electronic devices P. For example, the wireless transmission module 9 is disposed on the circuit substrate 10 and electrically connected to the circuit substrate 10, and the wireless transmission module 9 can be a smartphone or a tablet computer. In addition, the wireless transmission module 9 can be configured to wirelessly transmit the concentration and time trajectory information C-T to the at least one electronic device P. Therefore, the gas concentration signal S1, the user motion signal S6 or the concentration and time trajectory information C-T can be wirelessly transmitted to the at least one electronic device P by the wireless transmission module 9 (such as BLUETOOTH®) so as to inform relevant people that carry the electronic device P.

Beneficial Effects of the Embodiments

In conclusion, in the smart wearable device D provided by the present disclosure, by virtue of "the gas detection module 3 being disposed on the wearable device body 1 and electrically connected to the signal control module 2, for detecting a gas concentration of a predetermined gas surrounding the wearable device body 1 so as to obtain a gas concentration signal S1", "the signal recording module 4 being disposed on the wearable device body 1 and electrically connected to the signal control module 2, for recording a plurality of gas concentration values C that are provided by the gas concentration signal S1, and recording a plurality of gas-measuring time points T that are respectively configured for obtaining the gas concentration values C," and "the vibration generating module 5 being disposed on the wearable device body 1 and electrically connected to the signal control module 2, for generating a prompt signal S2 according to the gas concentration value C provided by the gas concentration signal S1, and generating a beat signal S3 according to a user setting value," the smart wearable device D can be configured to provide relevant information corresponding to the gas concentration signal S1, the prompt signal S2 and the beat signal S3 for the user that wears the smart wearable device D.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A smart wearable device, comprising:
  a wearable device body;
  a signal control module disposed on the wearable device body;
  a gas detection module disposed on the wearable device body and electrically connected to the signal control module, wherein the gas detection module is configured to detect a gas concentration of a predetermined gas surrounding the wearable device body so as to obtain a gas concentration signal;
  a signal recording module disposed on the wearable device body and electrically connected to the signal control module, wherein the signal recording module is configured to record a plurality of gas concentration values that are provided by the gas concentration signal, and record a plurality of gas-measuring time points that are respectively configured for obtaining the gas concentration values;
  a vibration generating module disposed on the wearable device body and electrically connected to the signal control module, wherein the vibration generating module is configured to generate a prompt signal according to the gas concentration value provided by the gas concentration signal, and generate a beat signal according to a user setting value;
  a signal display module disposed on the wearable device body and electrically connected to the signal control module, wherein the signal display module is configured to provide a display signal according to the gas concentration signal;
  an audio generating module disposed on the wearable device body and electrically connected to the signal control module, wherein the audio generating module is configured to provide an audio signal according to the gas concentration signal;
  a motion sensing module disposed on the wearable device body and electrically connected to the signal control module, wherein the motion sensing module is configured to provide a user motion signal according to a user motion trajectory of a user that wears the smart wearable device; and
  a wireless transmission module disposed on the wearable device body and electrically connected to the signal control module, wherein the wireless transmission module is configured to wirelessly transmit the gas concentration signal and the user motion signal to at least one electronic device.

2. The smart wearable device according to claim 1,
  wherein the gas detection module includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal, and the signal display module is configured to display the gas concentration value of the gas concentration signal that is detected by the gas detection module;
  wherein, when the gas concentration values and the gas-measuring time points match with each other to form concentration and time trajectory information, the signal display module is configured to display the concentration and time trajectory information, and the wireless transmission module is configured to wirelessly transmit the concentration and time trajectory information to the at least one electronic device;
  wherein the motion sensing module includes a gyroscope, an accelerometer, a magnetometer, and a barometer, and is configured to provide a user walking number and a user height value according to the user motion trajectory of the user that wears the smart wearable device, and the signal control module is configured to obtain user calorie consumption of the user that wears the smart wearable device according to the user walking number and the user height value.

3. The smart wearable device according to claim 1,
  wherein, when the gas concentration value provided by the gas concentration signal is less than a first preset value, the prompt signal generated by the vibration generating module is an unvibrated signal that is configured to stop generating vibration by the vibration generating module;
  wherein, when the gas concentration value provided by the gas concentration signal is greater than the first preset value and less than a second preset value, the prompt signal generated by the vibration generating module is a weak vibration or a short vibration that is generated by controlling the vibration generating module;
  wherein, when the gas concentration value provided by the gas concentration signal is greater than the second preset value, the prompt signal generated by the vibration generating module is a strong vibration or a long vibration that is generated by controlling the vibration generating module.

4. The smart wearable device according to claim 1,
  wherein, when the gas concentration value provided by the gas concentration signal is less than a first preset value, the display signal generated by the signal display module includes a first color message and a first animation message;
  wherein, when the gas concentration value provided by the gas concentration signal is greater than the first preset value and less than a second preset value, the display signal generated by the signal display module includes a second color message and a second animation message;

wherein, when the gas concentration value provided by the gas concentration signal is greater than the second preset value, the display signal generated by the signal display module includes a third color message and a third animation message;

wherein an eye opening percentage of a first blinking animation of the first animation message is greater than an eye opening percentage of a second blinking animation of the second animation message, and the eye opening percentage of the second blinking animation of the second animation message is greater than an eye opening percentage of a third blinking animation of the third animation message.

5. The smart wearable device according to claim 1, wherein, when the user setting value is set according to music information, the beat signal provided by the vibration generating module includes a musical beat message that is displayed by the signal display module, and a musical beat vibration that is generated by controlling the vibration generating module;

wherein, when the user setting value is set according to rhythm information, the beat signal provided by the vibration generating module includes a rhythmic beat message that is displayed by the signal display module, and a rhythmic beat vibration that is generated by controlling the vibration generating module;

wherein, when the user setting value is set according to walking information, the beat signal provided by the vibration generating module includes a walking beat message that is displayed by the signal display module, and a walking beat vibration that is generated by controlling the vibration generating module.

6. A smart wearable device, comprising:

a wearable device body;

a signal control module disposed on the wearable device body;

a gas detection module disposed on the wearable device body and electrically connected to the signal control module, wherein the gas detection module is configured to detect a gas concentration of a predetermined gas surrounding the wearable device body so as to obtain a gas concentration signal;

a signal recording module disposed on the wearable device body and electrically connected to the signal control module, wherein the signal recording module is configured to record a plurality of gas concentration values that are provided by the gas concentration signal, and record a plurality of gas-measuring time points that are respectively configured for obtaining the gas concentration values; and a vibration generating module disposed on the wearable device body and electrically connected to the signal control module, wherein the vibration generating module is configured to generate a prompt signal according to the gas concentration value provided by the gas concentration signal, and generate a beat signal according to a user setting value.

7. The smart wearable device according to claim 6, further comprising:

a signal display module disposed on the wearable device body and electrically connected to the signal control module, wherein the signal display module is configured to provide a display signal according to the gas concentration signal;

a motion sensing module disposed on the wearable device body and electrically connected to the signal control module, wherein the motion sensing module is configured to provide a user motion signal according to a user motion trajectory of a user that wears the smart wearable device; and a wireless transmission module disposed on the wearable device body and electrically connected to the signal control module, wherein the wireless transmission module is configured to wirelessly transmit the gas concentration signal and the user motion signal to at least one electronic device;

wherein the gas detection module includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal, and the signal display module is configured to display the gas concentration value of the gas concentration signal that is detected by the gas detection module;

wherein, when the gas concentration values and the gas-measuring time points match with each other to form concentration and time trajectory information, the signal display module is configured to display the concentration and time trajectory information, and the wireless transmission module is configured to wirelessly transmit the concentration and time trajectory information to the at least one electronic device;

wherein the motion sensing module includes a gyroscope, an accelerometer, a magnetometer, and a barometer, and is configured to provide a user walking number and a user height value according to the user motion trajectory of the user that wears the smart wearable device, and the signal control module is configured to obtain user calorie consumption of the user that wears the smart wearable device according to the user walking number and the user height value.

8. The smart wearable device according to claim 6, further comprising:

a signal display module disposed on the wearable device body and electrically connected to the signal control module, wherein the signal display module is configured to provide a display signal according to the gas concentration signal;

a motion sensing module disposed on the wearable device body and electrically connected to the signal control module, wherein the motion sensing module is configured to provide a user motion signal according to a user motion trajectory of a user that wears the smart wearable device; and a wireless transmission module disposed on the wearable device body and electrically connected to the signal control module, wherein the wireless transmission module is configured to wirelessly transmit the gas concentration signal and the user motion signal to at least one electronic device;

wherein, when the gas concentration value provided by the gas concentration signal is less than a first preset value, the prompt signal generated by the vibration generating module is an unvibrated signal that is configured to stop generating vibration by the vibration generating module;

wherein, when the gas concentration value provided by the gas concentration signal is greater than the first preset value and less than a second preset value, the prompt signal generated by the vibration generating module is a weak vibration or a short vibration that is generated by controlling the vibration generating module;

wherein, when the gas concentration value provided by the gas concentration signal is greater than the second preset value, the prompt signal generated by the vibration generating module is a strong vibration or a long vibration that is generated by controlling the vibration generating module.

9. The smart wearable device according to claim 6, further comprising:

a signal display module disposed on the wearable device body and electrically connected to the signal control module, wherein the signal display module is configured to provide a display signal according to the gas concentration signal;

a motion sensing module disposed on the wearable device body and electrically connected to the signal control module, wherein the motion sensing module is configured to provide a user motion signal according to a user motion trajectory of a user that wears the smart wearable device; and a wireless transmission module disposed on the wearable device body and electrically connected to the signal control module, wherein the wireless transmission module is configured to wirelessly transmit the gas concentration signal and the user motion signal to at least one electronic device;

wherein, when the gas concentration value provided by the gas concentration signal is less than a first preset value, the display signal generated by the signal display module includes a first color message and a first animation message;

wherein, when the gas concentration value provided by the gas concentration signal is greater than the first preset value and less than a second preset value, the display signal generated by the signal display module includes a second color message and a second animation message;

wherein, when the gas concentration value provided by the gas concentration signal is greater than the second preset value, the display signal generated by the signal display module includes a third color message and a third animation message;

wherein an eye opening percentage of a first blinking animation of the first animation message is greater than an eye opening percentage of a second blinking animation of the second animation message, and the eye opening percentage of the second blinking animation of the second animation message is greater than an eye opening percentage of a third blinking animation of the third animation message.

10. The smart wearable device according to claim 6, further comprising:

a signal display module disposed on the wearable device body and electrically connected to the signal control module, wherein the signal display module is configured to provide a display signal according to the gas concentration signal;

a motion sensing module disposed on the wearable device body and electrically connected to the signal control module, wherein the motion sensing module is configured to provide a user motion signal according to a user motion trajectory of a user that wears the smart wearable device; and a wireless transmission module disposed on the wearable device body and electrically connected to the signal control module, wherein the wireless transmission module is configured to wirelessly transmit the gas concentration signal and the user motion signal to at least one electronic device;

wherein, when the user setting value is set according to music information, the beat signal provided by the vibration generating module includes a musical beat message that is displayed by the signal display module, and a musical beat vibration that is generated by controlling the vibration generating module;

wherein, when the user setting value is set according to rhythm information, the beat signal provided by the vibration generating module includes a rhythmic beat message that is displayed by the signal display module, and a rhythmic beat vibration that is generated by controlling the vibration generating module;

wherein, when the user setting value is set according to walking information, the beat signal provided by the vibration generating module includes a walking beat message that is displayed by the signal display module, and a walking beat vibration that is generated by controlling the vibration generating module.

* * * * *